Figure 2:
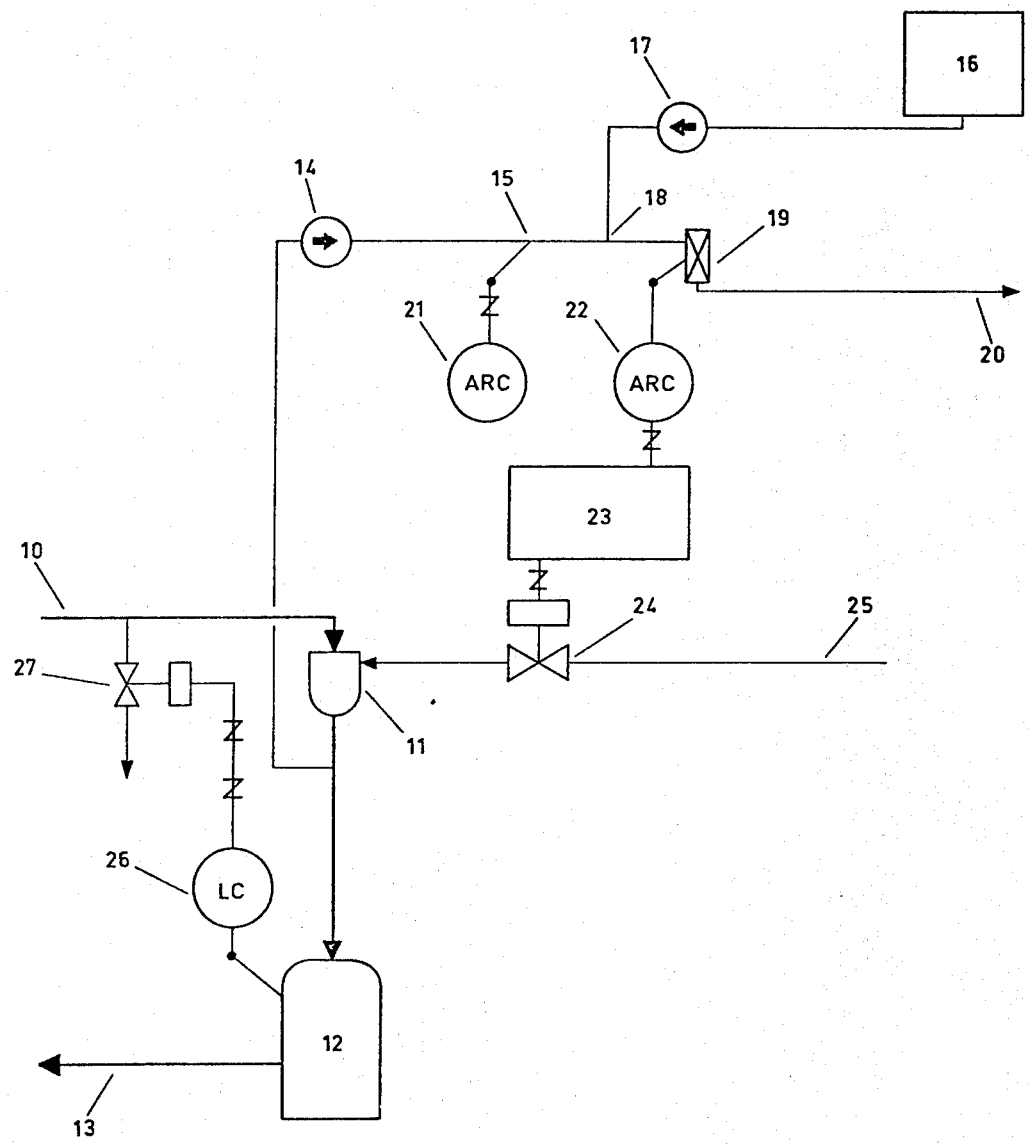

United States Patent [19]
Laxen

[11] 3,972,792
[45] Aug. 3, 1976

[54] DEVICE FOR DETERMINATION OF CHEMICALS IN A SAMPLE FLOW

[75] Inventor: Torolf Tom Paul Laxen, Helsinki, Finland

[73] Assignee: Oy Keskuslaboratorio-Centrallaboratorium AB, Tapiola, Finland

[22] Filed: Apr. 8, 1974

[21] Appl. No.: 458,790

[30] Foreign Application Priority Data
Apr. 17, 1973   Finland .............................. 1234/73

[52] U.S. Cl. ........................... 204/195 R; 204/1 T; 204/275
[51] Int. Cl.² ......................................... G01N 27/46
[58] Field of Search ....... 204/195 R, 195 G, 195 M, 204/1 T, 275, 149, 278

[56] References Cited
UNITED STATES PATENTS

| | | | |
|---|---|---|---|
| 1,505,104 | 8/1924 | Moerk ................................ | 204/149 |
| 2,768,135 | 10/1956 | Adelson .......................... | 204/195 R |
| 2,884,366 | 4/1959 | Anderson........................ | 204/195 R |
| 3,464,908 | 9/1969 | Donaldson..................... | 204/195 G |
| 3,464,910 | 9/1969 | Krebs et al........................ | 204/275 |
| 3,732,159 | 5/1973 | Platt............................... | 204/195 R |
| 3,755,124 | 8/1973 | Frant et al. ...................... | 204/195 G |
| 3,767,046 | 10/1973 | Hartkorn ......................... | 204/149 |

*Primary Examiner*—T. Tung
*Attorney, Agent, or Firm*—Woodling, Krost, Granger & Rust

[57] ABSTRACT

The present invention discloses an apparatus for the determination of chemicals in a sample flow, which includes in combination a hollow conical chamber having large and small diameter portions. An entrance conduit communicates with the large diameter portion of the chamber to introduce a sample flow into the chamber in a generally tangential direction and the sample travels in a generally spirally extending path to the small diameter portion. A first axially extending conduit is connected to the small diameter portion to provide for the exit of a heavier fraction of the sample flow from the conical chamber. A second exit conduit is connected in an axial manner to the large diameter portion of the conical chamber to exit a lighter fraction of the sample flow from the conical chamber. First and second spaced electrodes are positioned in the first exit conduit.

4 Claims, 6 Drawing Figures

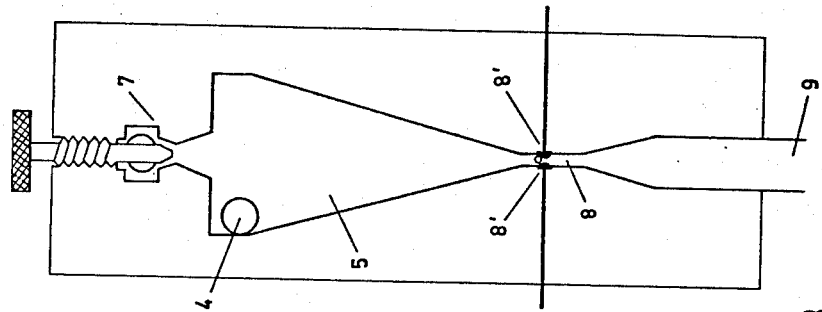
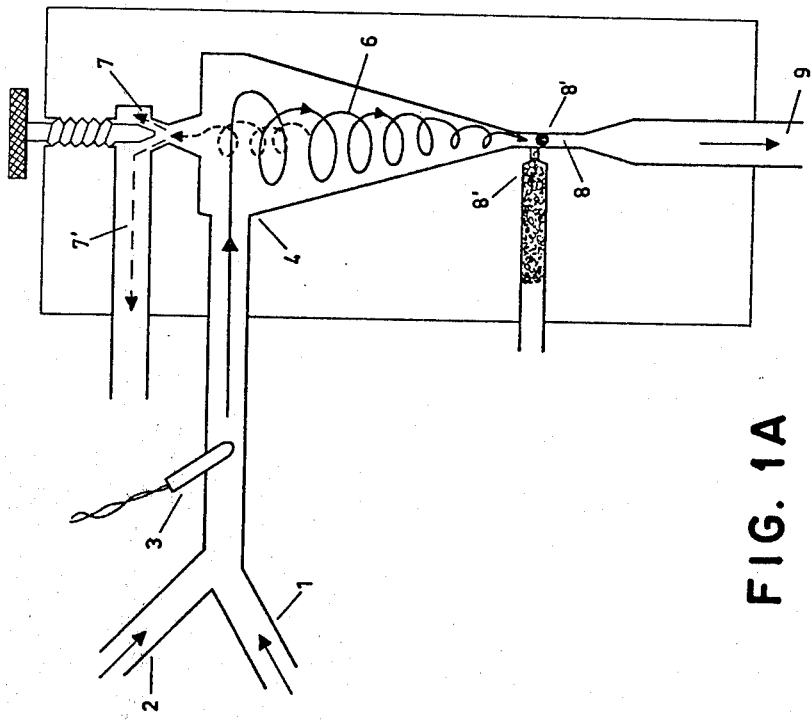
FIG. 1B
FIG. 1A

DEVICE FOR DETERMINATION OF CHEMICALS IN A SAMPLE FLOW

The present invention concerns a device for the determination of chemical concentrations in a sample flow. The device is applicable in connection with a method for a continuous control of recirculable pulp bleaching solutions. The control method is especially applicable for rapid bleaching methods characterized by the so-called "flow-through principle", but it is equally suited for the control of conventional bleaching systems.

Great difficulties have been encountered in the search into simple, automatic control methods for the present tower bleaching. Especially at the initial stages of bleaching, whereby the varying lignin content of the incoming unbleached pulp has to be levelled, the charge of right amounts of chemicals has proved to be most difficult. The classical way to approach the correct charge has required; the determination of the lignin content of the pulp in the laboratory; and the tracing of the residual chlorine in the initial bleaching by the application of redox electrodes. As a result, the charge of chlorine introduced into the bleaching is corrected as indicated by these analyses.

However, during the recent years continuously operating modifications of such analysing methods have been developed that have been applied with varying success for the control and steering of the bleaching processes. These include various coulometric, colorimetic and voltametric methods of analyses. Methods are used to monitor the consumption of chlorine in the initial bleaching and the brightness in the final bleaching. Process computer monitors additionally the consistensies of the pulps, the flows, the temperatures and charges chlorine and hypochlorite accordingly.

The present steering methods are not applicable for the very rapid bleaching methods of a new type which are characterized by large, excessive amounts of chemicals and by extensive recirculation of solutions. The present steering method is based on the continuous determination of concentrations of oxidizing and reducing chemicals in a sample flow of spent solutions. A part of the spent solution is automatically replaced with new strong chemical solution in accordance with the determinations, and the part of the solution replaced is removed from the process or it replaces, in turn, part of the spent liquor from some other point of the multistage bleaching process. The method can be accomplished by the installation of the new electrode chamber as described by the present invention.

If the concentration of the oxidizing agent is determined by the application of a voltametric measuring method, which maintains a constant voltage, the common equation for electrolysis is valid in the following form at certain present constant voltages:

$$i_{lim} = n F A D \cdot \frac{C}{\delta} \quad (1)$$

where $i_{lim}$ = so-called limit current of the current to be measured $n$ = number of electrones participating in the reaction $F$ = Faraday constant $A$ = surface area of the electrode $D$ = diffusion constant for the oxidizing (reducing) chemical in the solution $C$ = concentration of the oxidizing (reducing) substance in the solution $\delta$ = thickness of the diffusion layer.

In this kind of an electrochemical reaction the velocity of the movement of the substance is a very important factor. There are three basic mechanisms for the mass transport:

1. The movement of ions in a solution is dependent on the electrical gradients in the solution, whereby the ion move towards an electrode posessing an opposite charge. Then, on the electrode a Helmholz's layer is formed from ions bound electrostatically. The influence of such a phenomenon on the measurement can be reduced by the application of introduction of supporting electrolyte or substance which is electrochemically more inert than the other electrolytes in the solution.

2. Diffusion is a movement caused by the concentration gradient. During the electrolysis such concentration gradients of different substances are formed on the surface of the electrode. The diffusion layer ($\delta$) constantly increases reaching no limiting value.

3. Mechanical and thermal movement increases the movement of the substance and reduces and stabilies the diffusion layer.

In addition to the mechanisms of mass transport the temperature influences in different ways the measurement. The strength of the electrical current ($i_{lim}$) depends on temperature at a set value of the potential. This includes both the diffusion and the dependences related to the Nernst equation. Additionally, the temperature influences also the viscosity of the sample solution.

In the following, mentions are due to the requirements posed for a system of process control with regard to practical conditions and to the electrochemical theory described above.

A cell for a through-flow has to accommodate the following:

the gas bubbles commonly ocurring in the sample flow can be removed prior to the electrodes the construction is simple and easily serviced (self cleaning)

the mixing of the supporting electrolyte into the sample flow takes place evenly the flow rate of the sample in the chamber can be increased to result in a thin and stable diffusion layer which allows small fluctuations to occur in the actual sample flow without concurrent effect on the measurement the system can be coupled with a thermocompensator and a heat exchanger, if needed.

The object for the present invention is composed of a common flow-through chamber applicable for process conditions and especially for voltametric measurements. The features of an instrumentation fullfilling these requirements posed for the patent are described in patent claim 1.

The structure of the cell and the method are illustrated in the following with a reference to the drawings attached. The illustrations are the following:

FIG. 1a: the construction of the electrode chamber viewed from side

Figure 3:
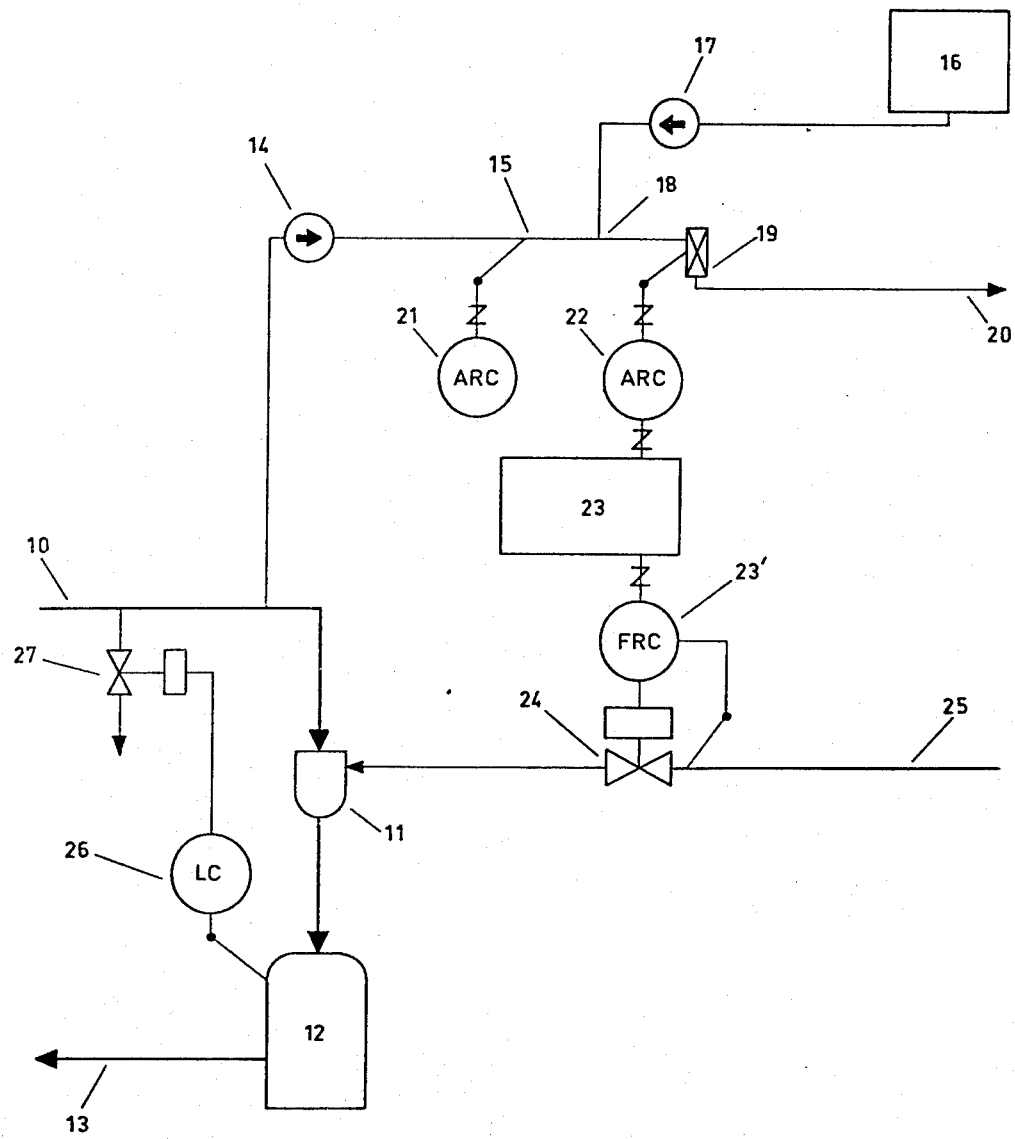
Figure 4:
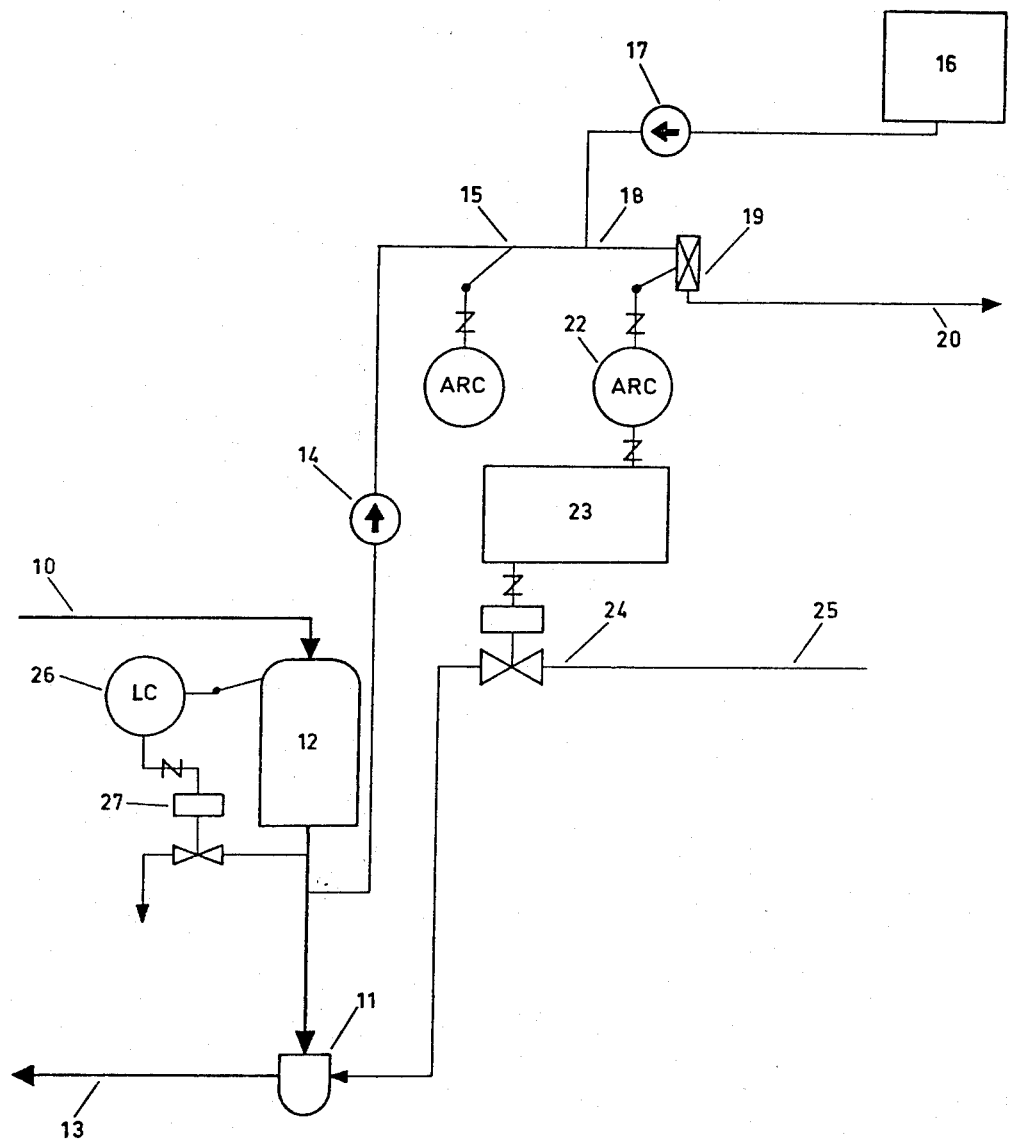
Figure 5:
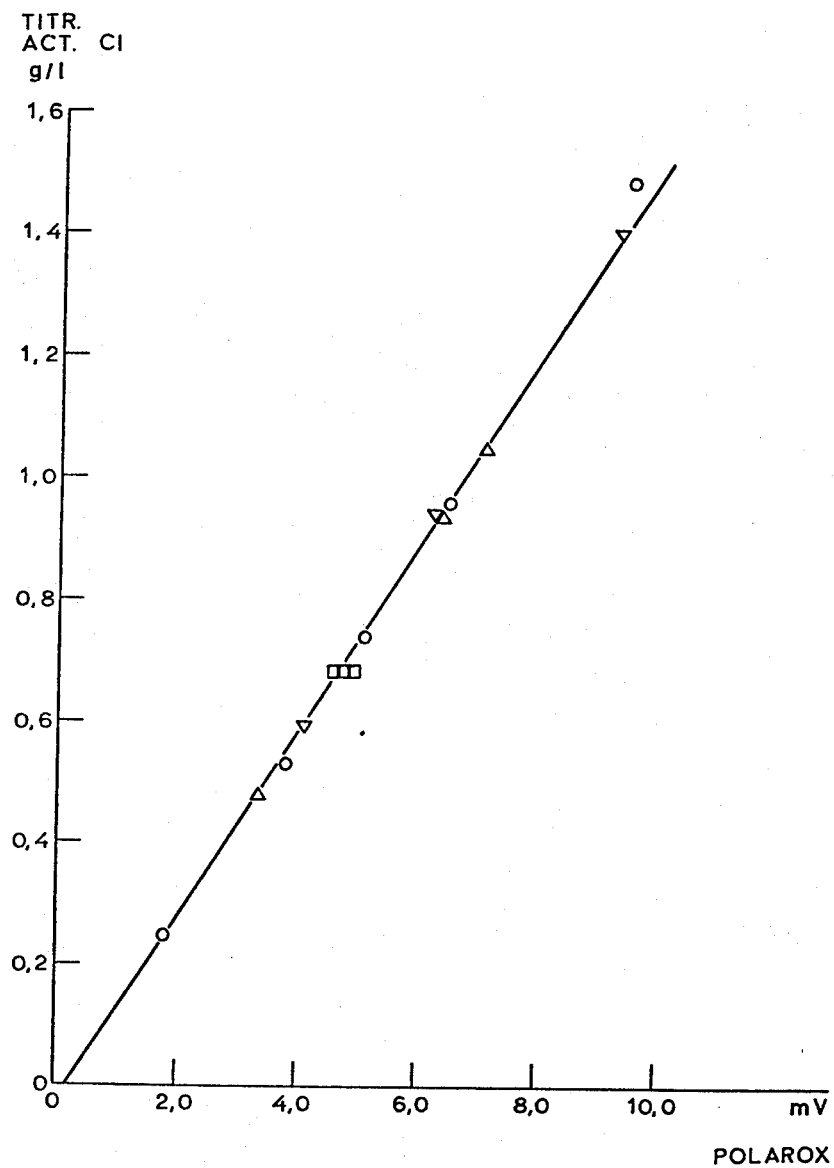

FIG. 1b: same as the prious figure but the view is taken at a right angle to FIG. 1a FIG. 2: principle of the steering method of bleaching
FIG. 3: same as FIG. 2, but with a different coupling
FIG. 4: same as FIG. 3, but with a different coupling
FIG. 5: concentrations of chlorine chemicals as recorded by the measuring system The construction and working principles of the electrode chamber are seen in FIG. 1. The sample flows in the tube 1 in the direction shown by the arrow. From the T-tube 2 supporting electrolyte solution flows over the tips of thermocompensator 3. At point 4 the sample flows tangentially to the bottom of the electrode cone 5 in the manner shown by the arrow and is forced in the cone into a turbulence as shown by arrow 6. In the cone the velocity is increased and due to the centrifugal force the gas bubbles rise from the middle part of the chamber upwards in the manner shown by the broken line arrows 6' and are removed through the needle valve 7. The sample flows into the narrow tube 8 located at the tip of the cone where the electrodes 8' are also located. As the flow rate increases at an inversely proportional relation to the areas of the cross sections of the tubes 1 and 8, such a fast flow-rate is accomplished at the measuring point 8 that the diffusion layer remains stable and the equation (1) can be written in the form $i_{lim} = M_v \, n \, F \, A \, D \, C$, where $M_v$ is a constant for mass transport. The sample flow is removed through tube 9.

The chamber can be used in the following manner:

Through the T-tube 2 it is possible to feed solvent B which markedly differs in regard to the specific weight from the initial sample solution A and is not mixable with it. This solvent B dissolves certain ions from solution A. Depending on the relative specific weight, the solvent is removed from the chamber either through the needle valve 7 and the tube 7' or through tube 8 and 9 in to the directions shown by the arrows. A needle valve is adjustable in such a way that the original solution A is forced through the opposite tube. For example, if the solution B is removed through tube 7', solution A is removed through tubes 8 and 9 and if solution A is removed through tube 7', solution B is removed through tubes 8 and 9. Electrodes are couplable also beyond the needle valve 7 in the tube 7'.

By application of such a measurement instrumentation it is possible to materialize the steering system according to FIG. 2. In tubes 10 the oxidizing spent liquor from bleaching flows into a storage tank 12 and further to bleaching 13. Prior to that, tank tube 10 is connected to mixing chamber 11 where fresh, strong oxidant is mixed with the spent liquor. By application of the level indicator 26 the valve 27 is set in such a way that an appropriate amount of spent liquor is either removed from the process or it in turn replaces a part of a spent liquor from some other stage of a multistage bleaching. After the mixing chamber 11 the bleaching liquor tube is provided with a sampling outlet, which provides by the application of a pump 14 a small sample flow through the pH-electrode chamber 15 into the subtube 18 which is introduced with an supporting electrolyte from tank 16 by application of the pump 17. The sample flows further through the electrode chamber 19 as described earlier into the sewer 20. Both pH and the voltametric measurements can be registered with recording instruments 21 and 22. The voltametric meter 22 is connected through a regulator unit 23 to an automatic valve 24, which regulates the volume flow of the oxidant to be added into the mixing chamber 11 from the tube 25. The regulating unit 23 is given a preset constant value whereby an even and desirable concentration of the bleaching liquor can be maintained in storage tank 12 by application of the valve 24.

It is characteristic for a fast through-flow bleaching that in a well controlled bleaching system a good correlation is obtainable for the relationship between the lignin content of a pulp and the consumption of active chlorine. The difference between the preset and the measured value is in a linear relationship to the variations occurring in the consumption and the lignin content.

Furthermore, a mention is due that at the final bleaching even a more simple control system is applicable for the flow through bleaching, since by virtue of the short reaction times involved the bleaching may be steered in such a manner that the differences in the lignin contents of the pulps can be levelled already of the beginning of the bleaching. Then also the consumption of chemicals is even.

The steering system described above is applicable for the circulation of oxidizing bleaching agents. However, the system is equally applicable also for reducing bleaching liquors. Disregarding the voltametric meter and by installing a pH meter instead the alkalinity of the bleaching may be measured.

The system illustrated in FIG. 3 differs from the previous one in the respect that the sample intake is placed in tube 10 prior to the mixing chamber 11. Recording flowmeter 23 measures the volume flow of the fresh chemical in tube 25. This modification provides means for direct measurement of chemical consumption.

FIG. 4 provides a third modification for the steering system. It differs from the first alternative due to the fact that the spent liquor flows directly into the storage tank 12. Measurement and the regulation of the concentration takes place when the solution returns back to the bleaching. By these means the autocatalyzed decomposition of the chemical can be diminished in the storage tank 12.

EXAMPLE

The purpose of this example is to show how the electrode chamber described above operates in connection with the measurement of chlorine chemicals when coupled to the Polarox instrument. It has been established that the preset constant potential of + 300 mV is preferable when measurements are done on solutions of both chlorine and chlorine dioxide with pH ≤ 2. When it is known that hypochlorite is converted to molecular chlorine at this pH-value, the following solution was devised.

Hydrochloric acid was regarded as the most preferable electrolyte due to the fact that it both increases the amount of chlorine ions and introduces a suitable pH. The supporting electrolyte may be, as well, spent liquor from the chlorination stage from which chlorine has been removed. The thermal effect was eliminated by application of a heat exchanger through which the sample flow was forced.

The electrode chamber was constructed according to FIG. 1. The diameter of tube 1 was 6 mm and that of tube 8 was 2 mm. The effective area of platinum electrodes was 1.6 mm² and their internal distance 0.9 mm. The flow-rate in the tube 8 was 1.8 m/s which is sufficient to hold the diffusion layer δ constant. It has been established that for example chlorine dioxide maintains a linear dependence between $i_{lim}$ and the concentration up to about 1 g active chlorine per liter. The dilution with a hydrochloric acid of 1% w/w in a proportion of 1:1 the linear area was widened. The temperature of the sample was 20° C in the chamber. The salt bridge of the calomel electrode was under 0.8 kp/cm² pressure.

| Chemical | | Titrated active chlorine gpl | recorder output mV |
|---|---|---|---|
| ○ | NaOCl | 0.25 | 1.80 |
| | | 0.53 | 3.80 |
| | | 0.74 | 5.10 |
| | | 0.96 | 6.50 |
| | | 1.49 | 4.50 |
| □ | NaOCl + NaCl | 0.78 + 0.0 | 4.90 |
| | | 0.78 + 10.0 | 4.70 |
| | | 0.88 + 20.0 | 4.60 |
| △ | $ClO_2$ | 0.48 | 3.40 |
| | | 0.93 | 6.30 |
| | | 1.05 | 7.10 |
| ▽ | $ClO_2^-$ | 0.59 | 4.10 |
| | | 0.93 | 6.30 |
| | | 1.40 | 9.30 |

FIG. 5 illustrates the values registered by the Polarox-instrument as a function of the titrimetric values.

The markings ○ □ △ ▽ in the table above and in FIG. 5 related to the table refer to the series of experiments.

From the table and the figure it is obvious that both accuracy and linearity are good. A mention is due that chlorine water is measurable at the same scale as the chemicals in the figure. A mention is due that Polarox-instrument is not capable of measuring chlorate as such modification.

The invention is not limited within the examples provided but it may vary considerably within the ranges of the patent claims.

What is claimed is:

1. Apparatus for the determination of concentrations of chemicals by means of a voltametric method in a sample flow including in combination a hollow conical chamber having an upper large diameter portion and a lower small diameter portion, entrance conduit means communicating with said large diameter portion to introduce a sample flow into the upper portion of said conical chamber in a generally tangential direction where it travels in a generally spiraling path to said lower small diameter portion, a first exit conduit axially connected to said small diameter portion of said conical chamber, outside and below the conical chamber, to exit a heavier portion of said sample flow from said conical chamber, a second exit conduit axially connected to said large diameter portion of said conical chamber, above the conical chamber, to exit a lighter portion of said sample flow from said conical chamber and first and second spaced measurement electrodes positioned inside said first exit conduit immediately adjacent said small diameter portion of said conical chamber.

2. Apparatus as claimed in claim 1, wherein an adjustable valve is positioned in said second exit conduit to regulate the flow therethrough.

3. Apparatus as claimed in claim 2, wherein T-tube conduit means is connected to said entrance conduit means to introduce a chemical composition into said sample flow.

4. Apparatus as claimed in claim 3, wherein a thermocompensator is interposed in said entrance conduit means.

* * * * *